United States Patent
Kumar et al.

(10) Patent No.: US 8,771,198 B2
(45) Date of Patent: Jul. 8, 2014

(54) SIGNAL PROCESSING APPARATUS AND METHOD FOR PHONOCARDIOGRAM SIGNAL

(75) Inventors: Prashant Kumar, Eindhoven (NL); Kumara Sanjaya, Eindhoven (NL); Souri Rajan Venkatesan, Eindhoven (NL); Yogisha Mallya, Eindhoven (NL)

(73) Assignee: Koninklijkle Philips N.V., Eindhoven (NL)

(*) Notice: Subject to any disclaimer, the term of this patent is extended or adjusted under 35 U.S.C. 154(b) by 0 days.

(21) Appl. No.: 13/515,739

(22) PCT Filed: Dec. 13, 2010

(86) PCT No.: PCT/IB2010/055768
§ 371 (c)(1),
(2), (4) Date: Jun. 13, 2012

(87) PCT Pub. No.: WO2011/073879
PCT Pub. Date: Jun. 23, 2011

(65) Prior Publication Data
US 2012/0289849 A1     Nov. 15, 2012

(30) Foreign Application Priority Data
Dec. 18, 2009 (EP) ..................... 09179922

(51) Int. Cl.
A61B 5/02 (2006.01)
A61B 7/04 (2006.01)
A61B 7/00 (2006.01)
A61B 5/0452 (2006.01)

(52) U.S. Cl.
CPC . *A61B 7/04* (2013.01); *A61B 7/005* (2013.01); *A61B 5/0452* (2013.01)
USPC ........................................ 600/528

(58) Field of Classification Search
USPC ............................ 600/528; 607/17
See application file for complete search history.

(56) References Cited

U.S. PATENT DOCUMENTS

| | | | |
|---|---|---|---|
| 5,687,738 A * | 11/1997 | Shapiro et al. ............ 600/528 |
| 6,572,560 B1 | 6/2003 | Watrous et al. | |
| 7,300,405 B2 | 11/2007 | Guion et al. | |
| 2005/0090755 A1 | 4/2005 | Guion et al. | |
| 2008/0154144 A1* | 6/2008 | Unver et al. ............... 600/528 |
| 2008/0234594 A1 | 9/2008 | Brooks et al. | |

OTHER PUBLICATIONS

Ari, S. et al, "DSP implementation of a heart valve disorder detection system from a phonocardiogram signal", Journal of Medical Engineering & Technology, vol. 32, No. 2, Mar. 2008, pp. 122-132, XP002633696, ISSM: 0309-1902.

(Continued)

*Primary Examiner* — Rex R Holmes

(57) ABSTRACT

A signal processing apparatus includes a phonocardiogram interface configured to receive a phonocardiogram signal captured according to a first set of capturing properties, a processor configured to analyze the phonocardiogram signal to determine an analysis result for the phonocardiogram signal and a confidence value of the determined analysis result, and a flow control configured to determine, whether a subsequent capture of the phonocardiogram signal according to a second set of capturing properties is likely to improve an accuracy of the determined analysis result. If applicable, the flow control coordinates the subsequent capture of the phonocardiogram signal according to the second set of capturing properties.

15 Claims, 8 Drawing Sheets

(56) References Cited

OTHER PUBLICATIONS

Marshal et al, "Signal analysis of medical acoustic sounds with applications to chest medicine", Journal of the Franklin Institute, vol. 344, No. 3-4, Mar. 27, 2007, pp. 230-242, ISSN: 0016-0032.

Ari, S. et al, "A robust heart sound segmentation algorithm for commonly occurring heart valve diseases", Journal of Medical Engineering and Technology, vol. 32, No. 6, Nov. 1, 2008, pp. 456-465, XP009147404, ISSN: 0309-1902.

Malarvini et al, "Heart sound segmentation algorithm based on instantaneous energy of electrocardiogram, Computers in Cardiology", 2003, pp. 327-330.

Lehner et al, "A Three-Channel Microcomputer System for Segmentation and Characterization of the Phonocardiogram", IEEE Transactions on Biomedical Engineering, vol. BME-34, No. 6, p. 489.

Gerbarg et al, "Analysis of phonocardiogram by a digital computer", Circulation Research, ISSN: 0009-7330, vol. 11, p. 569-576, 1962.

Liang, H et al, "A heart sound segmentation algorithm using wavelet decomposition and reconstruction", Engineering in Medicine and Biology Society, Proceedings of the 19th Annual International Conference of the IEEE, vol. 4, 1997, pp. 1630-1633.

Gamero, L.G. et al, "Detection of the first and second heart sound using probabilistic models", Engineering in Medicine and Biology Society, Proceedings of the 25th Annual International Conference of the IEEE, 2003, vol. 3, pp. 2877-2880, ISBN: 9780780377899.

Orman S. et al, "A heart sound segmentation and feature extraction algorithm using wavelets", Control, Communications and Signal Processing, 2004, First International Symposium on Control, Communication and Signal Processing, p. 235-238.

Sharif S. et al, "Analysis and classification of heart sounds and murmurs based on the instantaneous energy and frequency estimations", TENCON 2000 Proceedings, 2, pp. 130-134.

* cited by examiner

| Pathology | Symptoms & associated weightage | Essential Examinations | Similar Pathologies |
|---|---|---|---|
| Pathology A | X (10%), y (30%), z (60%) | Exam 1, exam2 | Pathology M and N |
| ... | ... | ... | ... |
| ... | ... | ... | ... |
| Pathology Z | X1 (35%), y1 (25%) | Exam N, exam N-1 | Patholology X |

Fig.5

| Cardiac Event | Timing, duration | Grade | Severity | Associated Pathologies | Best Auscultation location |
|---|---|---|---|---|---|
| Primary heart sound S1 | X, y, z | grade 1, grade 2 | Level 1 | A, B | Apex |
| ... | ... | ... | ... | ... | ... |
| ... | ... | ... | ... | ... | ... |
| Diastole | X1, y1, z1 | grade N grade N-1 | Level N | M, N | Pulmonary |

Fig.6

SIGNAL PROCESSING APPARATUS AND METHOD FOR PHONOCARDIOGRAM SIGNAL

FIELD OF THE INVENTION

The field of the present invention relates to a signal processing apparatus for automatic evaluation of a phonocardiogram signal. The field of the present invention also relates to a method of operation of a signal processing apparatus for automatic evaluation of a phonocardiogram signal. Furthermore, the field of the present invention relates to a computer program product comprising instructions that enable a processer to carry out a method of operation of a signal processing apparatus for processing a phonocardiogram signal.

BACKGROUND OF THE INVENTION

The examination of heart sounds provides a good and well proven way to assess the physical condition of the heart of a patient during a physical examination. In its classical form, the examination of heart sounds only requires a stethoscope and a physician who is experienced in interpreting the sounds he or she hears. By placing the stethoscope at different positions on the chest of the patient, it is possible to filter out different components of the heart sound. Thus, the heart sound may be separated into its components because the complete heart sound is produced by several sound sources distributed in and around the heart. The heart valves produce the most perceptible sounds. Another source of heart sounds is turbulent flow of blood which produces so called heart murmurs.

The frequency of primary heart sounds lies in the low frequency region where the sensitivity of the human ear is low. The occurrence of closely spaced cardiac events within the short cycle duration of a non-stationary heart sound signal makes it difficult to analyze the heart sounds. Computer-aided digital signal processing methods have been used to overcome these limitations.

A number of methodologies have been reported for the acquisition and analysis of heart sounds and of phonocardiogram signals which may be understood as a representation of the heart sounds in some other format, for example recorded on paper, magnetic tape, or in a digital format stored by a data processing system. Many other kinds of representing a heart sound as a phonocardiogram signal (PCG) are also possible and shall be encompassed by the term phonocardiogram.

Some techniques for automatically evaluating a phonocardiogram signal follow a black box approach wherein the input is the PCG signal along with an auxiliary electrocardiogram (ECG) signal. The output is based purely on the statistical processing of the PCG signal and optionally the ECG signal. An example for automatic analysis of heart sounds is presented in the article "Heart sound segmentation algorithm based on instantaneous energy of electrocardiogram" by Malarvini et al., published in 2003 in "Computers in Cardiology", pages 327-330. In 1987, Lehner and Rangayyan wrote their article "A three channel microcomputer system for segmentation and characterization of the phonocardiogram", published in "IEEE Transactions on Biomedical Engineering", 34. As early as 1962, Gerbarg et al. published their article "Analysis of phonocardiogram by a digital computer" in "Circulation Research", 11, pages 569-576. When, in known techniques, an auxiliary ECG signal is used, the ECG signal usually only assists in segmenting the PCG signal.

In some cases the need of an auxiliary signal is eliminated or a different auxiliary signal is used but the analysis is still purely based on the content of the PCG signal.

Examples can be found in the following articles:

Liang H. et al. (1997): "A heart sound segmentation algorithm using wavelet decomposition and reconstruction", Engineering in Medicine and Biology society, 4, pp. 1630-1633.

Gamero L. G. and Watrous R. (2003): "Detection of the first and second heart sound using probabilistic models", Engineering in Medicine and Biology society, 25th Intl. Conf., pp. 2877-2880.

Omran S. and Tayel M. (2004): "A heart sound segmentation and feature extraction algorithm using wavelets", First Intl. symposium on control, communication and signal processing, pp. 235-238.

Sharif Z. et al. (2000): "Analysis and classification of heart sounds and murmurs based on the instantaneous energy and frequency estimations", TENCON 2000 Proceedings, 2, pp. 130-134.

The focus of the existing techniques is either to provide a better representation of the cardiac events of the PCG signal or to present an automatic classifier system to predict cardiac disorders. The quality of diagnosis of a cardiac disorder may be improved by combining the analysis of the PCG signal with additional information, such as biomedical parameters of the patient (age group, gender, average heart rate, medical history, physical signatures, etc.). U.S. Pat. No. 5,687,738 (Shapiro et al.) and U.S. Pat. No. 6,572,560 B1 (Watrous et al.) describe techniques for analyzing heart sounds that take into account the medical history of the patient.

United States Patent Application No. US2005/0090755A1 (Guion et al.) describes an analysis of auscultatory sounds using single value decomposition. The analysis iterates through known physiological conditions and their associated heart sounds. During each iteration a similarity measure between the captioned heart sounds and those heart sounds associated with the given physiological condition is determined. The analysis produces a result based on the most similar heart sound.

SUMMARY OF THE INVENTION

In diseases of the heart which exhibit a complex pathophysiological representation, it is important to consider all aspects of history and physical examination to arrive at a reasonably good set of differential diagnoses. The teachings disclosed herein fortify the aspects of clinical examination and diagnosis. All data is investigated and presented holistically to assist a physician in determining a set of differential diagnoses, which none of the currently employed PCG based diagnostic techniques are capable of.

The teachings disclosed herein provide an interactive interface to the user wherein, depending on the particular embodiment, the user can validate and correct the findings at each step of diagnosis. Based on the a-priori knowledgebase the apparatus or the method also prompts the user for required inputs if missing. The pathological predictions and their prediction accuracies are update based on user corrections and additional inputs. So, it acts as a decision support system which allows for an error correction mechanism to account for algorithmic inaccuracies. Also, the apparatus or the method can be used as a teaching assistant for primary healthcare as the rules of PCG analysis followed by an expert system are built into the system knowledgebase.

The scarcity of trained physicians and lack of cost-effective devices makes cardiac examination difficult in remote/ rural areas. The claimed system can be used as a cost-effective screening system; the physician only needs to collect relevant medical and PCG data (using a standard digital stethoscope) to feed to the system.

The system also allows for a learning mode wherein the error corrections provided by the clinical user on a case to case basis can be used to update the knowledgebase and adjust relative probabilities. The learning mechanism provides the flexibility to adjust the system to a particular way of diagnosis followed by a physician.

The inventors of the present invention have realized that an efficient way to a highly accurate and reliable result may be implemented as a rule based approach towards examination. In the context of the rule based approach pathological indications of a number of findings for symptoms may be either suppressed or strengthened by another symptom or evaluation parameter, if necessary.

It would be desirable to provide a signal processing apparatus that implements an efficient and/or flexible road map from an initial capture of a heart sound towards an ultimate result that may be indicative of a finding for the patient being examined. This desire and/or possible other desires are addressed by a signal processing apparatus comprising a phonocardiogram interface, a processor, and a flow control. The phonocardiogram interface is adapted to receive a phonocardiogram signal captured from a patient according to a first set of capturing properties. The processor is adapted to analyze the phonocardiogram signal and the first set of capturing properties to determine an analysis result for the phonocardiogram signal and a confidence value of the determined analysis result. The flow control is adapted to determine, based on at least one of the determined analysis result and the confidence value, whether a subsequent capture of the phonocardiogram signal from the patient according to a second set of capturing properties is likely to improve an accuracy of the determined analysis result, and if so to coordinate the subsequent capture of the phonocardiogram signal according to the second set of capturing properties.

The phonocardiogram interface may be adapted to receive the phonocardiogram signal in acoustic format, in electrical format, in an analogue format, in a digital format, as a vector or as a data stream, for example.

The purpose of the analysis performed by the processor is to find evidence of cardiac diseases, or (at least) to rule out a specific cardiac disease with a sufficiently high reliability. This may be achieved, for example, by comparing the phonocardiogram signal with a plurality of stored phonocardiogram signals, each of the stored phonocardiogram signals being associated with a specific physiological condition. The confidence value may be based, for example, on a measure of similarity between the captured phonocardiogram signal and the stored phonocardiogram signals. The signal processing apparatus may be configured to suggest terminating the examination of heart sounds if the confidence value for a determined analysis result is sufficiently high, and/or if a subsequent capture or several subsequent captures are not likely to improve the accuracy of the determined analysis result and/or the confidence value. The signal processing apparatus is not necessarily a compact device, but could also be a distributed system. The components of such a distributed system could be mutually connected by suitable connections, such as cables or wireless connections.

The flow control determines whether a subsequent capture should be performed in order to improve the determined analysis result. If so, the flow control also determines which kind of subsequent capture should be performed. Depending on which kind of subsequent capture should be performed the flow control may retrieve a set of capturing properties from a storage and may distribute configuration parameters associated with the set of capturing properties to the sub-units of the signal processing apparatus. It may be envisaged that the flow control or another element of the signal processing apparatus adapts the capturing properties and/or the configuration parameters depending on other data that may be available to the signal processing apparatus, such as the medical history of the patient, his/her age, weight etc. The flow control is intended to gradually direct the signal processing apparatus and/or a user of the signal processing apparatus towards an ultimate determined analysis result, if possible in an efficient manner.

It would also be desirable that the signal processing apparatus determines the analysis result on information other than the phonocardiogram signal. This desire and/or possible other desires are addressed by the signal processing apparatus further comprising a data interface adapted to receive patient data regarding the patient. The processor may be further adapted to consider the received patient data for determining the analysis result. Patient data, such as the age, the weight and the medical history of the patient, may provide valuable information for the determination of the analysis result. For example, it could be that the heart sounds of two different physiological conditions are similar so that it may be difficult to classify the captured phonocardiogram signal in one or the other physiological condition. The patient data may help to classify the captured phonocardiogram signal, for example because one (or several) of the physiological conditions can be ruled out due to information contained in the patient data. The data interface could be a keyboard, a pointing device such as a computer mouse, a display, a touch screen, a connection to a database, a general network connection, a disk drive, or a combination of these. This list is non-exhaustive.

It may also be desirable that the signal processing apparatus would assist in determining a probable cardiac disorder of the patient. This desire and/or possible other desires are addressed by the signal processing apparatus further comprising a knowledge base containing relations between symptoms and cardiac disorders. Symptoms are information that may be collected during an examination of a patient and may include features of the phonocardiogram signal, the phonocardiogram signal itself, and other pieces of information. The relations between the symptoms and the cardiac disorders may be simple yes/no-relations or another type of relation. In particular, the relations between the symptoms and the cardiac disorders may comprise a weighting factor representing an amount of correlation between a symptom and a cardiac disorder. The weighting factors may be obtained from statistical studies of cardiac disorders and their symptoms. It may be envisaged that the knowledge base is updateable by means of a connection to a central data centre to which the latest studies and study results are uploaded to be processed and made available to the public or to subscribers.

It may also be desirable that the signal processing apparatus would adapt to the manner in which the user of the signal processing apparatus usually proceeds. This desire and/or possible other desires are addressed by the signal processing apparatus further comprising a user interface adapted to receive user input, and the knowledge base being adapted to evaluate the user input and to modify the relations between the symptoms and the cardiac disorder according to the user input. For example, the signal processing apparatus might be used in a certain environment such as a children's medical unit or a retirement home. When examining children for cardiac disorders it is possible that the focus of the examination is different from the examination focus applied to aged people. By means of the user interface the user may override certain suggestions for further examination steps proposed by the signal processing apparatus. The reason for the user to do so may be that he/she would like to check for those cardiac disorders first that are more probable in view of the type of patient that is most commonly being examined in the medical facility at hand. By evaluating the user input the knowledge base may reconfigure its configuration so that the user modified configuration may be used in the future. The knowledge base may query the user, for example via the user interface, whether the user approves to such a reconfiguration.

The knowledge base may be adapted to implement a structured approach to a conclusion about a possible cardiac disorder. The knowledge base may be adapted to control the flow control according to the structured approach. A communication or interaction between the knowledge base and the flow control makes it possible that the structured approach is not fixed but rather adaptable to intermediate results obtained during the examination procedure. For example, the knowledge base may instruct the flow control to coordinate the subsequent capture according to a set of capturing properties provided by the knowledge base. The set of capturing properties may also be determined on the basis of information provided by the knowledge base. Thus, superfluous examination steps may be omitted.

It may also be desirable that the user would have the option to modify the capturing properties himself or herself. This desire and/or possible other desires are addressed by the signal processing apparatus further comprising a user interface adapted to receive user input, and by the flow control being adapted to evaluate the user input and to modify the second set of capturing properties according to the user input.

It would be desirable that the signal processing apparatus exploits the various options and choices for capturing heart sounds. This desire and/or possible other desires are addressed by at least one of the first set of capturing properties and the second set of capturing properties comprising an auscultation location. An educated choice of the auscultation location may provide a phonocardiogram with a heart sound that is usable for narrowing down the number of possible analysis results.

It may also be desirable to facilitate or improve the analysis of the phonocardiogram signal by providing data that is correlated with the phonocardiogram signal. This desire and/or possible other desires are addressed by the signal processing apparatus further comprising a gating interface adapted to receive a gating signal indicative of a segmentation of consecutive cardiac cycles. It may be that the phonocardiogram signal is weak or that it differs from a normal shape encountered at healthy individuals. Under these conditions it may difficult to determine the various phases of the heart cycle solely on the basis of the phonocardiogram signal alone.

It would also be desirable that the gating signal (if employed) is easy to detect and sufficiently correlated with the phonocardiogram signal. This desire and/or other desires are addressed by the gating signal being an electrocardiogram signal. Capturing an electrocardiogram signal is fairly easy to accomplish. The electrocardiogram (ECG) represents the electrical activity of the heart which controls the heart muscle and thus indirectly the blood flow through the heart.

With respect to another aspect of the teachings disclosed herein, it would be desirable that a signal processing apparatus for a phonocardiogram signal would provide a certain degree of interactivity to a user of the apparatus at various stages of the signal processing procedure. This desire and/or possible other desires are addressed by a signal processing apparatus comprising a phonocardiogram interface, a processor, and a user interface. The phonocardiogram interface is adapted to receive a phonocardiogram signal captured from a patient. The processor is adapted to analyze the phonocardiogram signal to determine an analysis result for the phonocardiogram signal. The user interface is adapted to present the captured phonocardiogram signal to a user of the signal processing apparatus. The user interface is also adapted to receive a user correction from the user pertaining to a data processing action performed by the processor on the captured phonocardiogram signal. The processor is further adapted to reanalyze the phonocardiogram signal based on the user correction.

The phonocardiogram signal may be presented to the user in a variety of ways, for example displaying in a visual manner or playing the phonocardiogram signal as a sound signal. In the visual case, the user may zoom into the displayed phonocardiogram signal. The phonocardiogram signal may also be presented as a time-frequency diagram produced for example by means of a Fast Fourier Transformation (FFT). In the case of an acoustic presentation of the phonocardiogram signal, the signal may be played at a slower speed, possibly with preservation of the pitch. The frequency of the signal may also be shifted to higher pitches at which the human ear is more sensitive.

The user correction may pertain to at least one of a segmentation and a classification of the captured phonocardiogram signal. Thus, the user may assist the segmentation of the phonocardiogram signal into different segments, as well as the classification of these segments and/or the entire phonocardiogram signal.

The teachings disclosed herein may also be used in the context of a method of operation of a signal processing apparatus for processing a phonocardiogram signal. The method comprises:

receiving the phonocardiogram signal captured from a patient according to a first set of capturing properties, analyzing the phonocardiogram signal and the first set of capturing properties, determining an analysis result for the phonocardiogram signal and a confidence value of the determined analysis result, determining whether a subsequent capture of the phonocardiogram signal from the patient according to a second set of capturing properties is likely to improve an accuracy of the determined analysis result, and coordinating the subsequent capture of the phonocardiogram signal according to the second set of capturing properties.

The proposed method of operation controls the cooperation of various sub-units of the signal processing apparatus and is a technical method. The proposed method could also control the cooperation of several components of a technical system, where the components are more or less remote one from the other. The method may further comprise guiding a user through or according to a structured approach to a conclusion about a possible cardiac disorder based on the determined analysis result.

The method may further comprise receiving a user input and modifying the structured approach according to the user input to adapt the structured approach to user preferences. The method may further comprise actions that correspond to the features described in the description and/or in the claims directed at the signal processing apparatus. For example, the method may comprise receiving patient data, evaluating a knowledge base containing relations between symptoms and cardiac disorders, receiving and evaluating user input to modify the relations between the symptoms and the cardiac disorders according to the user input, controlling a flow control according to the structured approach, and/or receiving a gating signal indicative of a segmentation of consecutive cardiac cycles. The method may comprise an action of presenting the captured phonocardiogram signal to the user and another action of receiving a user correction from the user. The user correction may pertain to a segmentation or a classification of the phonocardiogram signal or of parts thereof.

The teachings disclosed herein may also be used in the context of a computer program product comprising instructions that enable a processor to carry out a method of operation of a signal processing apparatus for processing a phonocardiogram signal. The method comprises:

- receiving the phonocardiogram signal captured from a patient according to a first set of capturing properties,
- analyzing the phonocardiogram signal and the first set of capturing properties,
- determining an analysis result for the phonocardiogram signal and a confidence value of the determined analysis result,
- determining whether a subsequent capture of the phonocardiogram signal from the patient according to a second set of capturing properties is likely to improve an accuracy of the determined analysis result, and
- coordinating the subsequent capture of the phonocardiogram signal according to the second set of capturing properties.

The apparatus and the method according to the teachings disclosed herein may embody a-priori knowledge about the 1) biomedical parameters of interest, 2) their correlation with the cardiac events and 3) the behavior of cardiac events and biomedical parameters with respect to various pathological conditions of the heart. The a-priori knowledgebase is developed based on the inputs of expert physicians and recommendations from standard clinical societies.

These and other aspects of the invention will be apparent from and illustrated with reference to the embodiments) described herein after.

BRIEF DESCRIPTION OF THE DRAWINGS

FIG. 5 shows a schematic table illustrating a first aspect of a knowledge base implemented in an embodiment of the signal processing apparatus according to the teachings disclosed herein.

FIG. 6 shows another schematic table of the knowledge base implemented in an embodiment of the signal processing apparatus according to the teachings disclosed herein.

DETAILED DESCRIPTION OF THE EMBODIMENTS

The invention will now be described on the basis of the drawings. It will be understood that the embodiments and aspects of the invention described herein are only examples and do not limit the protective scope of the claims in any way. The invention is defined by the claims and their equivalents. It will also be understood that features of an aspect can be combined with a feature of a different aspect or aspects.

Figure 1:
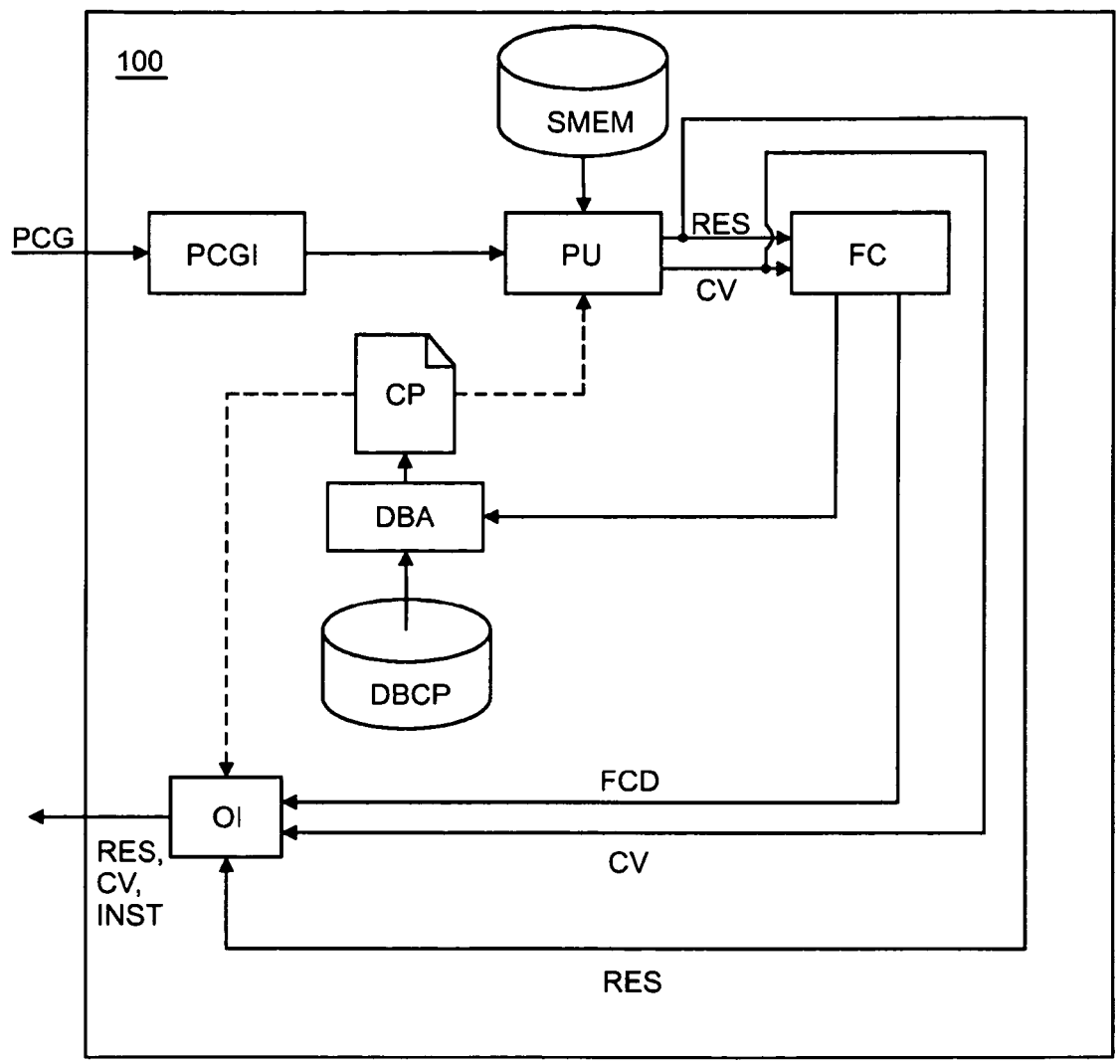
FIG. 1 shows a schematic block diagram of a signal processing apparatus according to the teachings disclosed herein.

FIG. 1 shows in a schematic manner a block diagram of a signal processing apparatus 100 according to the teachings disclosed herein. A phonocardiogram signal PCG is received at a phonocardiogram interface PCGI. The phonocardiogram interface PCGI may be an interface to a digital stethoscope, to a microphone adapted to capture the phonocardiogram signal, a microphone itself, or another suitable means for receiving the phonocardiogram signal PCG in a format in which the phonocardiogram signal PCG is available. The phonocardiogram signal PCG is forwarded to a processing unit PU (processor). The processing unit PU analyzes the phonocardiogram signal PCG for example by decomposing the phonocardiogram signal PCG in a frequency-time domain. Another possibility might be a wavelet analysis of the phonocardiogram signal PCG. The processing unit PU also receives capturing properties CP indicating under which circumstances the phonocardiogram signal PCG was captured. The capturing properties CP may include an auscultation location, an information about whether the patient was breathing or holding his breath, an information about whether the patient was resting or exercising prior to the examination, and/or other information. Based on the phonocardiogram signal PCG and the capturing properties CP the processing unit PU determines an analysis result RES. The determination of the analysis result RES may rely on a comparison of the phonocardiogram signal PCG with sample phonocardiogram signals stored in a sample memory SMEM of the signal processing apparatus 100. In the alternative or in addition to the comparison with sample phonocardiogram signals the processing unit PU may analyze the phonocardiogram signal PCG by extracting relevant features from the phonocardiogram signal PCG. These features could be maxima in the amplitude of the phonocardiogram signal, frequencies of sections of the phonocardiogram signal, number and temporal relationship of prominent sections in the phonocardiogram signal, etc. The processing unit PU may then match the determined features of the phonocardiogram signal PCG with predetermined thresholds or numeric ranges in order to arrive at the analysis result RES. The processing unit PU also calculates a confidence value CV indicating a level of confidence for the analysis result RES.

The analysis result RES and the confidence value are forwarded to an output interface OI. The output interface OI display the analysis result RES and the confidence value CV to a user of the signal processing apparatus 100. The output interface OI may be a display or a screen. It is also imaginable that the output interface OI informs the user acoustically about the analysis result RES and the confidence value CV.

The analysis result RES and the confidence value CV are also forwarded from the processing unit PU to a flow control FC. The flow control FC evaluates the analysis results RES and the confidence value CV to determine whether a subsequent capture of the phonocardiogram signal PCG from the patient is advisable. The flow control FC also determines whether changing the capturing properties CP is likely to improve the quality and accuracy of the determined analysis result RES. The flow control FC instructs a database access module DBA to load another set of capturing properties CP from a database of capturing properties DBCP if it has been determined that a subsequent capture using the other set of capturing properties CP is likely to improve the quality of the determined analysis result. Note that the analysis result RES determined previously may become void after the subsequent capture has been performed and the processing unit PU has analyzed the phonocardiogram signal PCG obtained during the subsequent capture. The flow control FC sends flow control data FCD to the output interface OI to inform the user of the signal processing apparatus 100 about the next action(s) that shall be performed. The output interface OI also receives the new set of capturing properties CP to be displayed to the user. In this manner the output interface OI may inform the user about necessary modifications in the capturing properties, such as a change of the auscultation location or whether the patient should be instructed to breath or to hold his breath.

The user may acknowledge that he has changed the capturing properties as suggested by the flow control FC in conjunction with the database of capturing properties DBCP. In the alternative, the processing unit PU may detect the change of the capturing properties performed by the user since the phonocardiogram signal PCG has changed or was absent for a short period of time.

The system or apparatus may accept the following inputs: 1) Biomedical parameters of the patient e.g. age, gender, patient history, physical symptoms etc., 2) Auscultation location i.e. the position of stethoscope on the patient's chest and 3) Segmented cardiac cycles of the PCG signal.

Clinical data for biomedical parameters can be obtained by physical examination of the patient and also from the patient's medical history. Heart sound recordings at different auscultation locations can be obtained using any standard digital stethoscope. The system (or apparatus) assumes segmented cardiac cycles at a given auscultation location as the input. In general, the cardiac cycles from the patient's heart sound recording can be extracted in a number of ways. For example 1) using an auxiliary ECG signal if present, 2) by using some other gating signal, 3) using signal processing methods alone without the need of an auxiliary signal, 4) by manual segmentation of heart sound recording etc.

The input heart sound cycles are processed by the system (or apparatus) to extract the cardiac features of interest. The system algorithms use standard digital signal processing and pattern classification techniques for heart cycle analysis. The biomedical information about the heart sound cycle e.g. average duration of systole, diastole, S1 and S2 etc. is also used for feature extraction. The cardiac features identified by the system are marked as annotations on the heart sound cycle to present a graphical display to the user.

The system maintains a knowledgebase in the form of tables as presented in FIGS. 5 and 6. The information about 1) various pathological conditions of the heart, 2) features of heart sound signal, 3) biomedical parameters of concern, 4) rules of PCG analysis and the correlation among these information pieces is maintained. This information along with the cardiac features extracted by the system algorithms is used to predict the pathological condition of the heart.

Based on the input clinical data the system evaluates the possible pathological conditions using the knowledgebase and the identified cardiac events. The clinical user is presented with the set of possible quantified predictions and the identified cardiac features. Using the knowledgebase the system also prompts the user if additional clinical inputs are required to strengthen a particular prediction or to resolve ambiguity between possible pathological conditions. The result set i.e. the quantified predictions are updated based on the additional clinical inputs provided by the user.

The system allows the clinical user to validate and correct the cardiac features obtained by the system algorithms. If the clinical user finds that a particular cardiac feature identified by the system is incorrect, the user can correct it. The user correction is accepted by the system and the predictions are re-evaluated accordingly. At the same time the system also learns from the user specified corrections by adjusting the internal relative probabilities in the knowledgebase.

Figure 2:
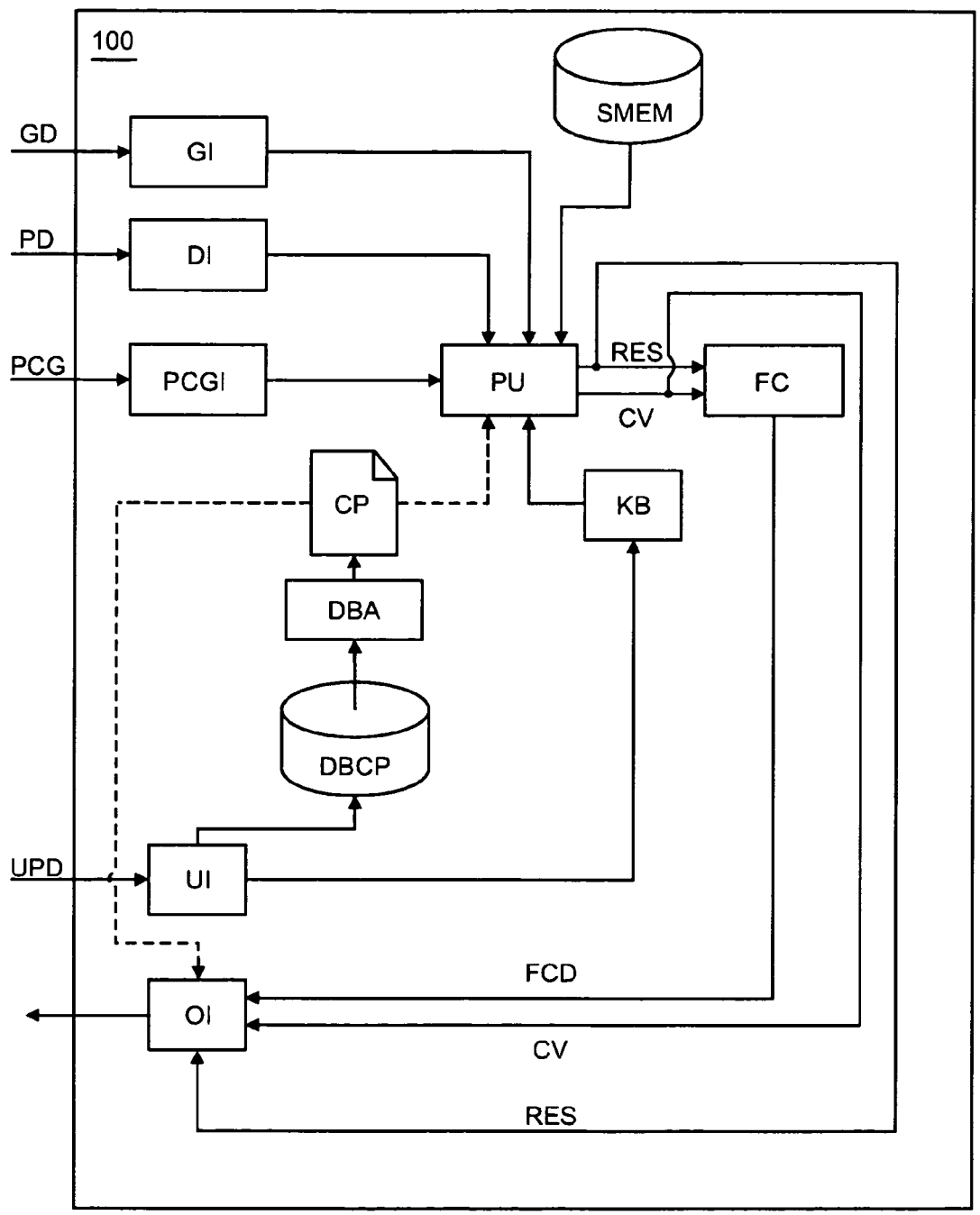
FIG. 2 shows a schematic block diagram of another embodiment of a signal processing apparatus according to the teachings disclosed herein.

FIG. 2 shows a schematic block diagram of another embodiment of the signal processing apparatus 100 according to the teachings disclosed herein. Elements that are shown in FIG. 1 and have been described above are not necessarily mentioned again in the following description of FIG. 2. Besides the elements already explained above, the embodiment of the signal processing apparatus 100 shown in FIG. 2 further comprises a knowledge base KB. The knowledge base KB contains relations between symptoms and cardiac diseases. These relations may be implemented as a numeric value called "weight". The knowledge base KB is connected to the processing unit PU so that the processing unit PU may compare the symptoms and properties detected in a phonocardiogram signal PCG with entries contained in the knowledge base KB. The signal processing apparatus 100 shown in FIG. 2 also comprises a data interface DI adapted to receive patient data PD. The data interface DI is connected to the processing unit PU to forward the patient data PD to the processing unit PU.

The knowledgebase KB assigns weightings i.e. confidence factors to various symptoms associated with cardiac disorders, which are used to quantify the accuracies of predictions by the system. These confidence factors can also be fine tuned by a clinical user as per his/her preference towards diagnoses.

The processing unit PU may identify the cardiac features of interest from the heart sound cycle using a combination of standard digital signal processing and pattern recognition techniques with the biomedical characteristics of the heart sound signal.

Patient information from all aspects like history, physical examination and investigations are considered holistically along with the cardiac signal features to arrive at a diagnosis. The correlation of all these aspects and their relative probabilities are taken into account for the quantified prediction of the pathologies.

Furthermore, the signal processing apparatus 100 shown in FIG. 2 comprises a gating interface GI adapted to receive gating data GD that may also be forwarded to the processing unit PU.

The processing unit PU may consider the phonocardiogram signal PCG, the patient data PD, the gating data GD, and the information provided from the knowledge base KB to determine the analysis result RES and the confidence value CV. The gating data GD assists in segmenting the phonocardiogram signal PCG. The patient data PD may cause a shift of some weighting factors used by the processing unit PU. For example, it may be possible that the knowledge base KB contains different records for patients of different age groups, such as children, adolescents, adults, and elderly people.

The signal processing apparatus 100 shown in FIG. 2 further comprises a user interface UI adapted to receive update data UPD from the user of the signal processing apparatus 100. The update data UPD contains input from the user that reflects the user's preferences regarding the sequence of the examination procedure and/or the content of the analysis result RES. The user interface UI is connected to the database of capturing properties DBCP and to the knowledge base KB. The update data UPD received from the user is forwarded to the database of capturing properties DBCP and/or the knowledge base KB so that these two elements of the signal processing apparatus 100 may update the data under which they operate. In this manner the user may teach the signal processing apparatus 100 for example to use a different set of capturing properties in a certain situation. The user may also configure the signal processing apparatus 100 to change the order or the priority of the subsequent captures. The signal processing apparatus 100 may thus be configured over time to the needs of the user and thus deliver more accurate results (at least as far as the configuration of the user may be regarded as being correct), possibly in less time.

Figure 3:
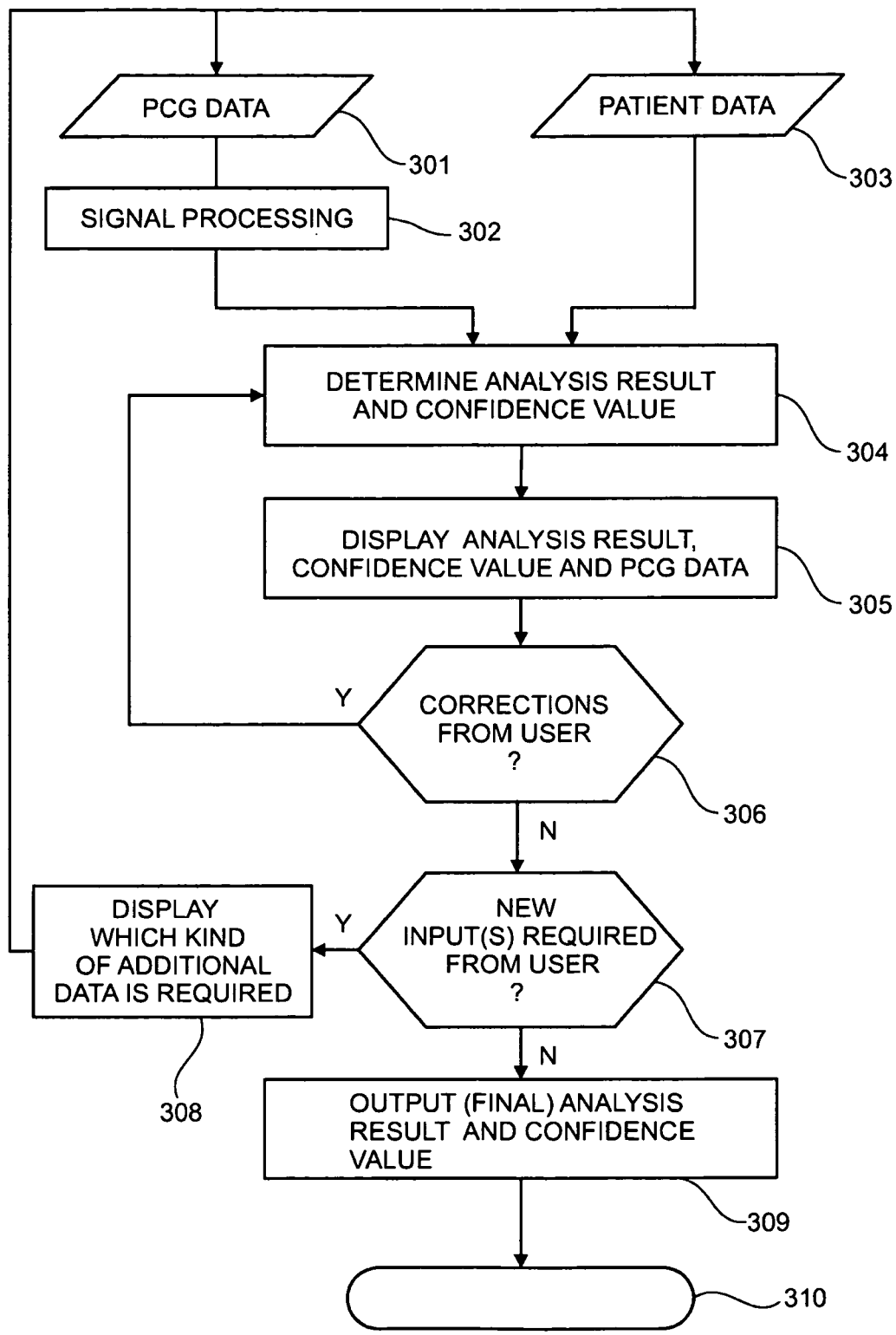
FIG. 3 shows a schematic flow chart of a method according to the teachings disclosed herein.

FIG. 3 shows in a schematic manner a flow chart of a method of operation for a signal processing apparatus according to the teachings disclosed herein. The method starts with two data records, namely a phonocardiogram data record 301 and a patient data record 303. The phonocardiogram record 301 undergoes signal processing at block 302. The signal processing 302 may comprise filtering, segmenting, and/or transforming the phonocardiogram data 301.

The signal processed phonocardiogram data 301 and the patient data both reach a block 304 in which an analysis result and a confidence value are determined. The determination of the analysis result and the confidence value may be based on a knowledge base containing relations between symptoms and cardiac diseases. The symptoms may be contained in the phonocardiogram data 301 or the patient data 303. Based on the inputs provided, the system may intelligently predict the pathological condition and provide a set of clinical findings and the associated quantification of the pathological possibilities. Using the knowledgebase system may also provide a checklist which notifies the clinical user to provide additional inputs if required to improve diagnostic accuracy. If additional inputs are provided, the system re-evaluates the clinical findings and the associated result set. Essentially this interactive mechanism allows the clinical user to filter down to the best possible prediction.

The determined analysis result and confidence value are displayed to the user at 305. Optionally, the phonocardiogram data 301 may also be communicated to the user or output to the user as an acoustic signal via a loudspeaker or headphones. In this manner, the user may get an idea of what the phonocardiogram signal PCG looks like or sounds like.

For example, the heart sound cycles may be graphically presented to the user and the identified cardiac features may be indicated on the graphical display as annotations. The other biomedical parameters of the patient may be presented in a tabular format.

The method and also the signal processing apparatus may provide an error correction mechanism. If the user finds that the automatic prediction of the system about the cardiac features is incorrect, the user can correct it. The system re-evaluates its findings and result set based on the user-correction. The error correction specified by the user is also considered as a learning input for the system and the knowledgebase and relative probabilities inside the system are updated to factor in these errors. The ability of the method and system to integrate user corrections and also learn from them makes it a flexible decision support system that mimics the diagnostic pattern followed by the physicians. This ability of the method and the system is illustrated in block 306 of FIG. 3 and in the following description relative thereto.

At a decision point 306 it is determined whether the user has entered any input that could be interpreted as a user correction of the displayed phonocardiogram's analysis. If so, the method loops back to block 304 in order to reanalyze the phonocardiogram signal taking into account the user correction(s) and to determine a new analysis result. The user correction may consist in e.g. moving automatically determined boundaries between two cycles of the phonocardiogram signal or between individual segments thereof. The user correction could also be a manual reclassification of certain automatically determined features of the phonocardiogram signal.

The system may also have the capability to capture other inputs e.g. ECG and Echo findings to build an increased knowledge base in order to cover a broader spectrum of pathologies with increased accuracy.

At the decision point 307 it is determined whether new input(s) is/are required from the user. These inputs may be another capture of the phonocardiogram signal PCG under different configuration properties or further information about the patient. The method proceeds to block 308 if it has been determined that new input(s) are indeed required from the user for providing a better analysis result and/or a higher confidence value. At 308 it is displayed to the user which kind of additional data is required. For example, the user may be instructed to reposition the microphone or the digital stethoscope to another location on the chest of the patient. The user may also be requested to ask the patient a particular question, such as whether the patient feels a pain in the chest. From block 308 the method branches back to the reception of the phonocardiogram data record 301 or to the reception of the patient data record 303. Note that either the phonocardiogram data record or the patient data record or both data records may be updated by the user. From there, the method starts a new iteration taking into account the updated information.

If at decision point 307 it has been determined that no new input(s) is/are required from the user, the method proceeds to block 309. The criteria for determining whether or not new inputs are required may comprise whether the confidence value is high enough, whether a confidence value of a second best analysis result is sufficiently smaller than the confidence value of the determined analysis result, whether the analysis result matches the provided patient data, and/or other suitable criteria. At block 309 the analysis result and the confidence value are output to the user. The method ends at block 310.

Figure 4:
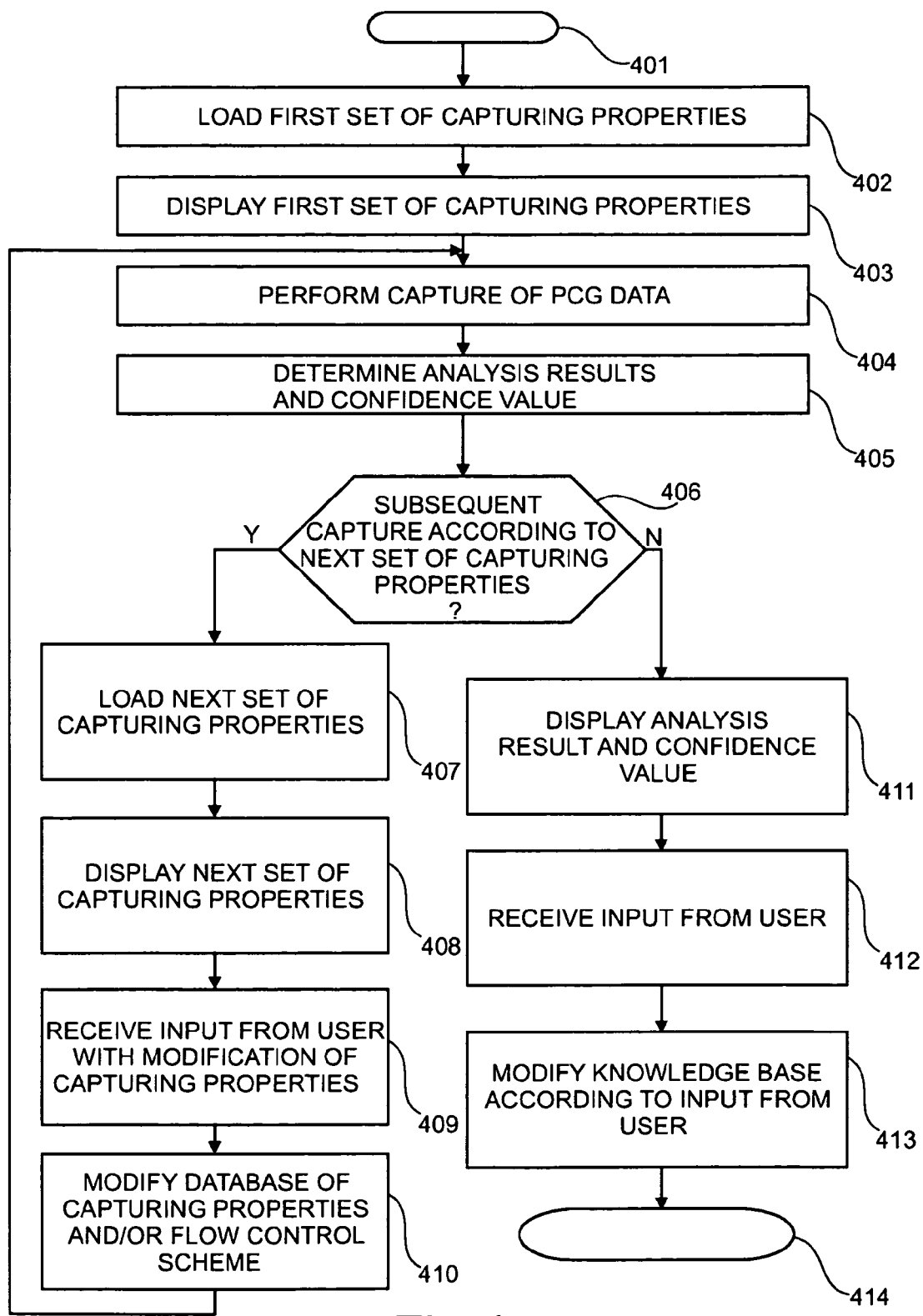
FIG. 4 shows a schematic flow chart of an aspect of a method of operation of a signal processing apparatus according to the teachings disclosed herein.

FIG. 4 shows another embodiment of the method of operation of a signal processing apparatus according to the teachings disclosed herein. The method starts at block 401. At block 402 a first set of capturing properties is loaded and at block 403 the first set of capturing properties is displayed. The user of the signal processing apparatus may now adjust an examination setup according to the displayed first set of capturing properties, e.g. placing a digital stethoscope at a location indicated by the first set of capturing properties. Then, at 404, the capture of the phonocardiogram data is performed. This may be initiated by the user pushing a button or by analyzing the captured phonocardiogram data. Analysis results and confidence values are determined at 405. At a decision point 406 it is determined whether a subsequent capture according to a next set of capturing properties is advisable. If so, the method continues at block 407 and loads the next set of capturing properties. The sets of capturing properties may be provided by a database of capturing properties DBCP. At block 408 the next set of capturing properties is displayed to the user so that the user may again adjust the examination setup according to the next set of capturing properties. Optionally, an input from the user with a modification of the capturing properties or a manual selection of a different set of capturing properties is received at block 409. Based on the received optional input from the user, the database of capturing properties DBCP and/or the flow control scheme followed by the flow control FC are modified at block 410. Then the method loops back to block 404 to perform the subsequent capture of phonocardiogram data according to the next set of capturing properties or the modified set of capturing properties.

The method proceeds to a block 411 if it has been determined at the decision point 406 that no subsequent capture according to a next set of capturing properties is advisable or necessary. At block 411 the determined analysis result and the confidence value are displayed to the user. Optionally, the user may input some modifications to the determined analysis result and/or the data that led to the determined analysis result. The user's modification is received at block 412 as an input from the user. At another optional block 413 of the flow chart shown in FIG. 4, the knowledge base is modified according to the input from the user. The method then ends at block 414.

As can be seen in the flow chart shown in FIG. 4, and especially the blocks 409, 410, 412, and 413 the method of operation of a signal processing apparatus offers a self-learning capability. Usually, the signal processing apparatus is shipped with a pre-configured structured approach that provides reliable analysis results for a majority of patients. If the signal processing apparatus 100 is used for similar types of patients over some period of time, and if the user modifies the database of capturing properties and/or the flow control scheme of the flow control FC, then the this embodiment of the signal processing apparatus 100 may adapt itself to the specific conditions of heart sound analysis encountered in the environment in which the signal processing apparatus 100 is used.

FIGS. 5 and 6 show tables of the knowledge base KB in an exemplary manner. The table shown in FIG. 5 shows how the relations between a cardiac disease ("Pathology") and symptoms may be represented. For example, relations exist between the pathology A and the symptoms X, y and z. The table shown in FIG. 5 also indicates the weighting factors for the symptoms when used to diagnose the pathology A. Accordingly, the symptom X has a relatively low weighting factor of 10%, symptom y has a slightly higher weighting factor of 30%, and symptom z has the highest weighting factor of 60%.

Furthermore, the table shown in FIG. 5 also indicates which examinations should be performed in order to reliably diagnose the pathology A. These are designated in FIG. 5 by the generic terms "Exam 1" and "Exam 2".

The last column of the table shown in FIG. 5 shows which pathologies are similar to a given pathology. In the case of the pathology A these are the pathologies M and N.

The table shown in FIG. 5 may be pre-filled with data available in medical data bases, medical text books, etc. Depending on whether user interactivity is supported by the signal processing apparatus or the method of operation of a signal processing apparatus, the content of the table may be updated by the user to better reflect preferences.

The table shown in FIG. 6 contains relations between cardiac events observable in a phonocardiogram signal and associated pathologies. For example, the primary heart sound S1 can be observed with a specific timing or duration X, y, z at a patient suffering from one of the pathologies A or B. Other columns in the table shown in FIG. 6 are the grade of the cardiac event, the severity, and the best auscultation location.

The table shown in FIG. 5 is most likely to be used be the flow control FC and the table shown in FIG. 6 may be used by the processing unit PU.

Figure 7:
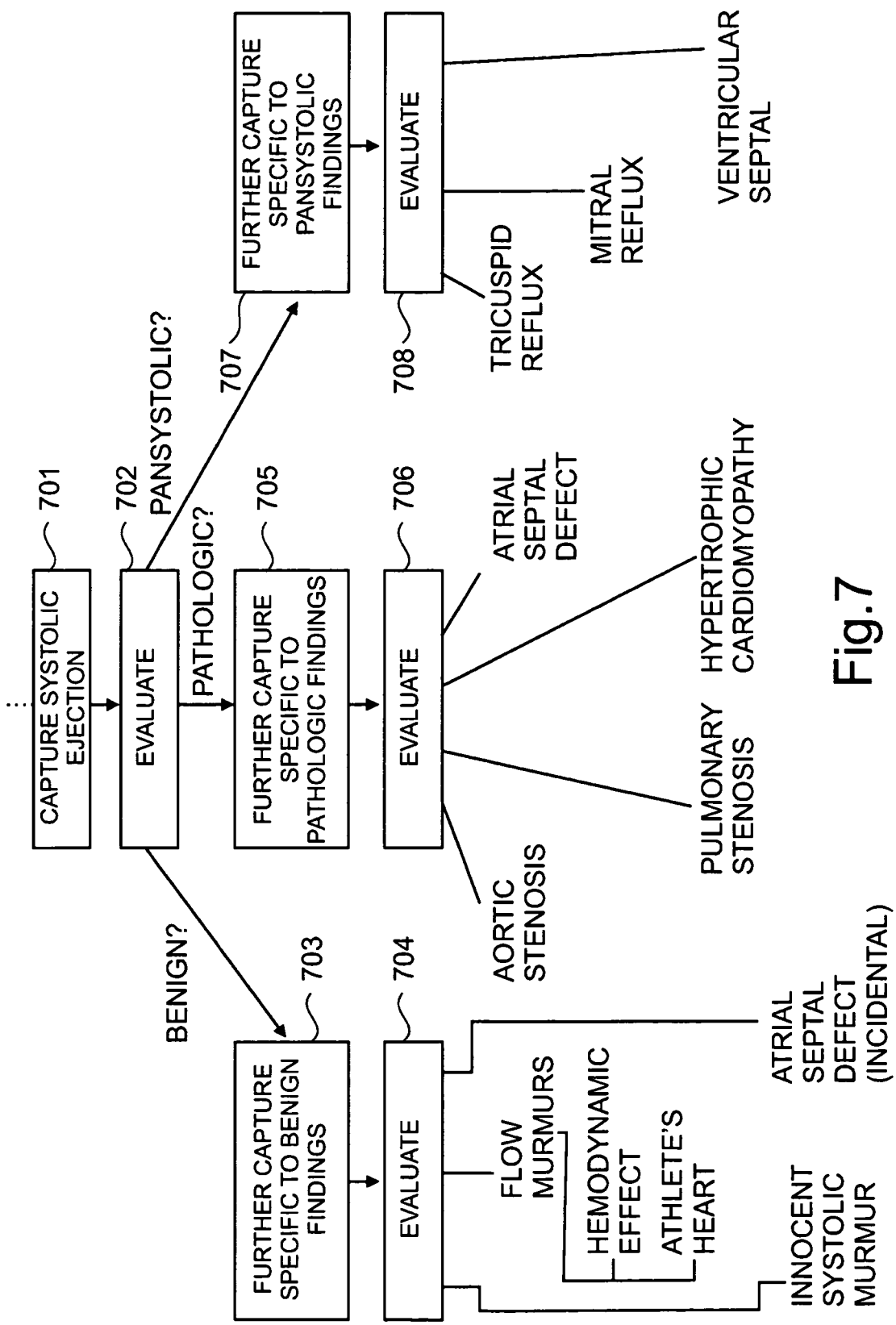
FIG. 7 shows a schematic and partial illustration of a structured approach according to the teachings disclosed herein.

FIG. 7 shows in a schematic manner a structured approach as implemented by the signal processing apparatus 100 and its method of operation. The structured approach is based on a differential diagnosis of systolic murmur. At a block 701 a capture of systolic ejection is performed. The result is evaluated by the processing unit at block 703. The processing unit is capable of classifying the captured phonocardiogram signal in one three classes. The classes are "benign", "pathologic", and "pansystolic".

Assuming that the processing unit has classified the phonocardiogram signal as "benign", the flow control FC coordinates a further capture which is specific to benign findings at block 703. After the further capture has been performed, the new phonocardiogram signal PCG is evaluated at block 704. The new phonocardiogram signal was optimized as to enable the processing unit PU to further classify the general benign finding. Therefore, the processing unit has a good chance of classifying the phonocardiogram signal in one of the following classes: 1) innocent systolic murmur, 2) flow murmurs, 3) atrial septal defect (incidental).

Further assuming that the second capture of the phonocardiogram signal has confirmed "flow murmurs" two further possibilities are now presented as the physiological condition. The first possibility is that the patient shows a hemodynamic effect (i.e., fever, hyperthyroidism, severe anemia). The second possibility is that the patient has an athlete's heart. A distinction between these two possibilities may require questioning the patient about symptoms associated with at least one of the two possibilities.

Going back to block 702 and now assuming that the captured phonocardiogram signal PCG indicates a pathologic condition, a further capture specific to pathologic finding is coordinated by the flow control FC at block 705. At block 706 the subsequently captured phonocardiogram signal PCG is evaluated to distinguish between the following four possibilities: 1) aortic stenosis, 2) pulmonary stenosis, 3) hypertrophic cardiomyopathy, 4) atrial septal defect.

In case a pansystolic condition has been detected at block 702, the structured approach guides the user to block 707 at which a further capture specific to pansystolic findings is coordinated and performed. At block 708 the finding are evaluated and classified into of the following possibilities: 1) tricuspid reflux, 2) mitral reflux, 3) ventricular septal.

It may be that the evaluation performed at block 702 is capable of indicating a trend towards one of benign finding, pathologic findings, or pansystolic finding. In this case, the structured approach may propose to coordinate and perform that subsequent capture of the phonocardiogram signal PCG first that is indicated by the trend or tendency.

Alternatively, the user may provide an input to the signal processing apparatus 100 that he would like to perform a capture specific to e.g. pansystolic findings first. If supported by the signal processing apparatus 100, the user's choice may be stored in the flow control FC so that from now on the signal processing apparatus will first propose to perform a capture specific to pan-systolic findings.

Figure 8:
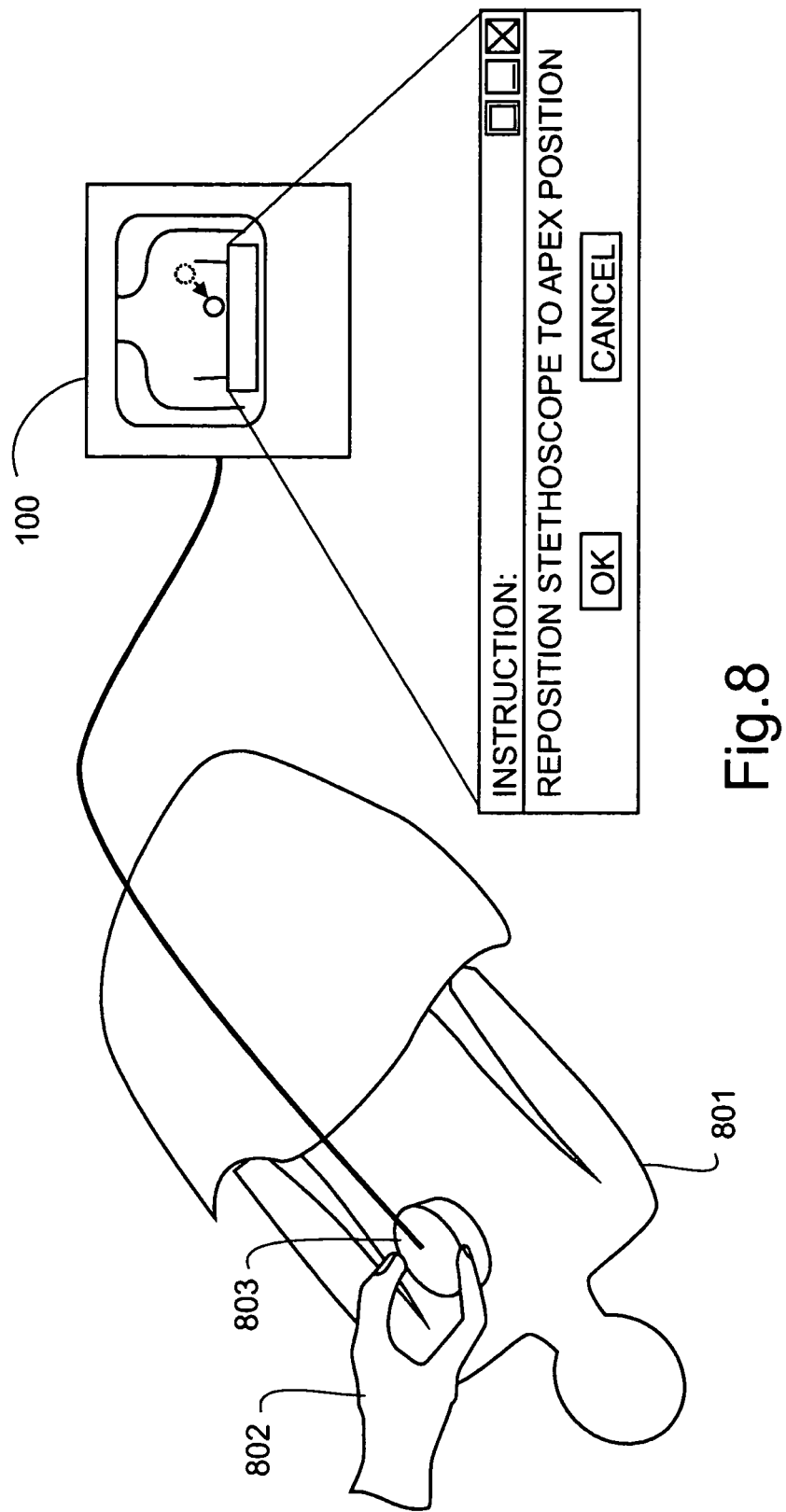
FIG. 8 shows an exemplary application of the signal processing apparatus according to the teachings disclosed herein.

FIG. 8 shows an exemplary application of the signal processing apparatus according to the teachings disclosed herein. A patient 801 is being examined by a user 802 (only the user's hand is illustrated), for example a physician or a nurse. The user 802 hold a digital stethoscope 803 in his hand and the digital stethoscope 803 is placed the patient's 801 chest. The digital stethoscope 803 is connected to the signal processing apparatus 100. The signal processing apparatus 100 comprises a display as the output interface OI (see FIGS. 1 and 2) showing a representative illustration of a patient's chest. The signal processing apparatus 100 is currently displaying an instruction to the user 802 to reposition the stethoscope from the current position to an apex position. The instruction is presented to the user as a text in a dialog box and also as a graphical illustration. When the user has repositioned the stethoscope to the suggested apex position, he may push the button "OK". The signal processing apparatus 100 will then perform the capture and the processing of the phonocardiogram signal. In the alternative, the user may click or push the button "Cancel". In response, the signal processing apparatus 100 may present a list of possibly other sets of capturing properties from which the user may select a set capturing properties that meets his requirements and preferences. The display area of the signal processing apparatus 100 may be a touch screen so that the user may simply touch the screen at the location of the icon that he wants to select. It may also be possibly to control the signal processing apparatus 100 via voice commands so that the user has both hands free.

Figure 9:
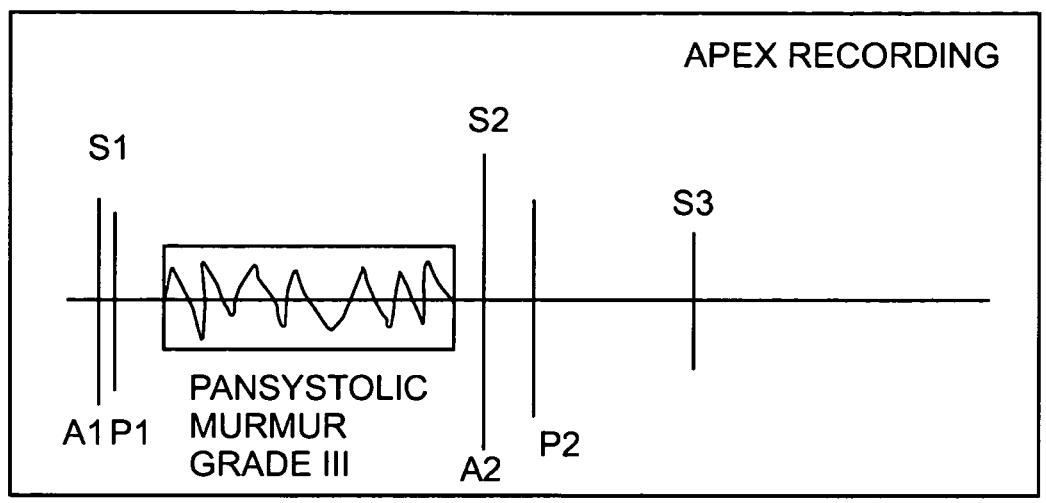
FIG. 9 shows an exemplary graphical representation of a phonocardiogram signal and corresponding annotations displayed by the signal processing apparatus.

FIG. 9 presents an example of the identification of cardiac events. This will be superimposed on top of the PCG cycle. If the user wants to correct the identification, he/she can select the particular event and edit it, e.g. can change "Pansystolic murmur Grade III" to "Mid systolic murmur Grade II". Likewise, the user can edit A2/P2 sequence for second heart sound if automatic identification is incorrect.

The user will be presented with the feature set as well. An example feature set is given below.
Patient biomedical features:
  Age
  Gender
  Avg. heart rate
  Patient history
  Physical symptoms
  . . . etc.
Cardiac event features:
  Auscultation Location
  Systole duration
  Diastole duration
  S3 (present /absent)
  S4 (present /absent)
  S1 split (normal/ abnormal)
  S2 split (normal/ abnormal)
  Systolic murmur (present /absent)
  Diastolic Murmur (present /absent)
  Systolic Murmur Shape
  Diastolic Murmur Shape
  Systolic Murmur Grade
  Diastolic Murmur Grade
  Opening Snap (present /absent)
  Ejection Click (present /absent)
  Mid systolic Click (present /absent)
  Mid diastolic click (present /absent)
  . . .
  etc.
Other features
  Geographical Location
  Race
  . . .
  etc.

Consider a case where the automated analysis suggests the following features for the PCG cycle of an adult at Apex location: Normal S1, Normal Split S2, absence of third and fourth heart sounds, ejection systolic murmur, no murmur in diastole.

The prediction of the system after first pass could be:

| Atrial Septal Defect | 30%, |
| Valvar Pulmonary Stenosis | 30%, |
| Innocent Pulmonary Flow murmur | 65%. |

The possible workflows after this are: The system might then prompt for PCG cycle at Pulmonary area. With this new input the system will check if the murmur is louder for Pulmonary area PCG cycle. If yes, it strengthens the prediction for all the pathologies as all of them exhibit loudest murmur in pulmonary area. So, the accuracies increase for all three predictions:

| Atrial Septal Defect | 35% |
| Valvar Pulmonary Stenosis | 35% |
| Innocent Pulmonary Flow murmur | 74% |

As the rules suggest, these three pathological cases are close in nature and the identification of normal or wide split S2 or systolic ejection click is extremely important for accurate prediction, it will prompt the physician to re-assure these features by visually examining the PCG cycle.

If the physician confirms the absence of wide split S2 and systolic ejection click, the prediction results will favor Innocent Pulmonary Flow murmur and suppress the other two possibilities

| Atrial Septal Defect | 5% |
| Valvar Pulmonary Stenosis | 5% |
| Innocent Pulmonary Flow murmur | 92% |

If the physician confirms the presence of wide split S2 and absence of systolic ejection click, the prediction results will favor Atrial Septal Defect

| Atrial Septal Defect | 89% |
| Valvar Pulmonary Stenosis | 5% |
| Innocent Pulmonary Flow murmur | 8% |

If the physician confirms the absence of wide split S2 i.e. S2 is normal and presence of systolic ejection click, the prediction results will favor Valvar Pulomonary Stenosis

| Atrial Septal Defect | 10% |
| Valvar Pulmonary Stenosis | 90% |
| Innocent Pulmonary Flow murmur | 8% |

This particular example demonstrates a possible workflow based on the features extracted from the cardiac cycle events. The system may capture the entire range of pathologies, their symptoms i.e. various cardiac and other biomedical feature and their correlation into the knowledge base. So, the system not only comes up with automatic predictions but also stresses on the important set of features (corresponding to possible pathological findings) and prompts the physician to evaluate them carefully. If the automatic analysis goes wrong, the decision support system provides the flexibility to accommodate physician's corrections and updates the predictions accordingly.

The described and illustrated device and method are potentially useful both in-hospital and out-of-hospital. Especially in remote place educated in diagnosing heart sounds is not readily available, the proposed signal processing apparatus and method offer a means for pre-screening patients.

The teachings disclosed herein describe a cost-effective PCG based automated classifier system for diagnosing cardiac disorders.

The scarcity of trained physicians and lack of cost-effective devices makes cardiac examination difficult in remote/rural areas of developing countries (emerging markets). The claimed system can be used as a cost-effective screening and diagnostic mechanism, in emerging markets where higher tech screening can be reserved for true-positive cases and the physician only needs to collect relevant medical and PCG data (using a standard digital stethoscope) to feed to the system.

It can be used as a decision support system for the clinicians to validate and support their diagnoses.

It can be used as a teaching assistant for heart sound examination and diagnoses.

One of the examples of usage of this system could also be in the pre-anesthesiology screening out-patient unit as well as similar units. Typically, in pre-anesthesiology screening, many patients are sent to the cardiology dept for ultrasound based on cardiac sound anomolies. (For example aortic stenosis is a major anesthesia risk, particularly in emerging markets where loco-regional, or ketamine based anesthesia is common for general surgery).

Other variations to the disclosed embodiments can be understood and effected by those skilled in the art in practicing the claimed invention from a study of the drawings, the disclosure, and the appended claims. In the claims, the word "comprising" does not exclude other elements or steps, and the indefinite article "a" or "an" does not exclude a plurality. A single processor or other unit may perform functions of several items recited in the claims, and vice versa. The mere fact that certain measures are recited in mutually different dependent claims does not mean that combinations of these measures cannot be used to advantage. Any reference signs found in the claims should not be construed as limiting the scope.

The invention claimed is:

1. A signal processing apparatus comprising:
   a phonocardiogram interface configured to receive a phonocardiogram signal captured from a patient in accordance with that signal's respective plurality of capturing properties selected from at least one of an auscultation location, information about the patient breathing or holding breath, information about the patient resting or exercising prior to the capture of the signal;
   a processor configured to analyze the first phonocardiogram signal using its respective plurality of capturing properties and to provide an analysis and a confidence value of the analysis; and
   a flow control configured
   to determine, based on at least one of the analysis and the confidence value, whether a subsequent phonocardiogram signal if captured from the patient according to a different plurality of capturing properties is likely to improve accuracy of the analysis, and if so
   to coordinate capture of the subsequent phonocardiogram signal from the patient according to the different plurality of capturing properties.

2. The signal processing apparatus according to claim 1, further comprising a data interface configured to receive patient data, wherein the processor is further configured to consider the received patient data for the analysis.

3. The signal processing apparatus according to claim 1, further comprising a knowledge base describing relations between patient's symptoms and cardiac disorders.

4. The signal processing apparatus according to claim 3, wherein the relations between the patient's symptoms and the cardiac disorders comprise a weighting factor representing an amount of correlation between a symptom and a cardiac disorder.

5. The signal processing apparatus according to claim 3, further comprising a user interface configured to receive user input, wherein the knowledge base is configured to evaluate the user input and to modify the relations between the symptoms and the cardiac disorders according to the user input.

6. The signal processing apparatus according to claim 3, wherein the knowledge base is configured to implement a structured approach to a conclusion about a possible cardiac disorder, and to control the flow control according to the structured approach.

7. The signal processing apparatus according to claim 1, further comprising a user interface configured to receive user input, wherein the flow control is configured to evaluate the user input and to modify the different plurality of capturing properties of the captured phonocardiogram signal according to the user input.

8. The signal processing apparatus according to claim 1, wherein at least one of the plurality of capturing properties and the different plurality of capturing properties comprises the auscultation location.

9. The signal processing apparatus according to claim 1, further comprising a gating interface configured to receive a gating signal indicative of a segmentation of consecutive cardiac cycles.

10. A signal processing apparatus comprising:
    a processor configured to analyze and provide a confidence value of the analysis of at least an initial and a subsequent phonocardiogram signals captured from a patient in accordance with each signal's respective plurality of capturing properties selected from at least one of an auscultation location, information about the patient breathing or holding breath, information about the patient resting or exercising prior to the capture of the signal;
    a user interface configured to receive a correction from the user pertaining to a data processing action, and segmentation and classification of the captured phonocardiogram signal,
    wherein the processor is further configured to generate a different plurality of capturing properties for capture of a subsequent phonocardiogram signal based on the user correction.

11. The signal processing apparatus according to claim 10, wherein the user correction pertains to at least one of segmentation and classification of portions of the captured phonocardiogram signal.

12. A method of operation of a signal processing apparatus for processing a first phonocardiogram signal, the method comprising acts of:
    receiving the first phonocardiogram signal captured from a patient in accordance with that signal's respective plurality of capturing properties selected from at least one of an auscultation location, information about the patient breathing or holding breath, information about the patient resting or exercising prior to the capture of the signal;
    analyzing the first phonocardiogram signal using its respective plurality of capturing properties to provide an analysis and a confidence value of the analysis;

determining, based on at least one of the analysis and the confidence value, whether a subsequent phonocardiogram signal if captured from the patient according to a different plurality of capturing properties is likely to improve accuracy of the analysis; and if so coordinating capture of the subsequent phonocardiogram signal from the patient according to the different plurality of capturing properties.

13. The method according to claim 12, further comprising an act of:

guiding a user according to a structured approach to a conclusion about a possible cardiac disorder based on the analysis.

14. The method according to claim 13, further comprising acts of:

receiving a user input; and modifying the structured approach according to the user input to adapt the structured approach to user preferences.

15. A non-transitory computer readable medium comprising computer instructions which, when executed by a processor, configure the processor to carry out a method of operation of a signal processing apparatus for processing a phonocardiogram signal, the method comprising acts of:

receiving the first phonocardiogram signal captured from a patient in accordance with that signal's respective plurality of capturing properties selected from at least one of an auscultation location, information about the patient breathing or holding breath, information about the patient resting or exercising prior to the capture of the signal;

analyzing the first phonocardiogram signal using its respective plurality of capturing properties to provide an analysis and a confidence value of the analysis;

determining, based on at least one of the analysis and the confidence value, whether a subsequent phonocardiogram signal if captured from the patient according to a different plurality of capturing properties is likely to improve an accuracy of the, analysis; and if so coordinating capture of the subsequent phonocardiogram signal according from the patient to the different plurality of capturing properties.

* * * * *